United States Patent [19]

Yarrington

[11] Patent Number: 5,198,457
[45] Date of Patent: Mar. 30, 1993

[54] TREATMENT OF HYPERTHYROIDISM WITH 1,3-DIHYDRO-1[2-(2-THIENYL)ALKYL]-2H-IMIDAZOLE-2-THIONES

[75] Inventor: John T. Yarrington, Worthington, Ohio

[73] Assignee: Merrell Dow Pharmaceuticals Inc., Cincinnati, Ohio

[21] Appl. No.: 870,527

[22] Filed: Apr. 17, 1992

[51] Int. Cl.$^5$ ............................................. A61K 31/415
[52] U.S. Cl. ..................................................... 514/392
[58] Field of Search .......................................... 514/392

[56] References Cited

U.S. PATENT DOCUMENTS 5,057,613 10/1991 Matthews et al. .................. 548/318

OTHER PUBLICATIONS

Ray W. Fuller, et al., New Inhibitors of Dopamine β-Hydroxylase, Advances in Enzyme Regulation, 1977, V15, pp. 267-281.

Primary Examiner—Frederick E. Waddell
Assistant Examiner—Zohreh A. Fay
Attorney, Agent, or Firm—Edlyn S. Simmons

[57] ABSTRACT

The use of 1-(thienylalkyl)imidazole-2-thione derivatives as antihyperthyroid agents are described herein. These compounds may be administered as a preparatory adjunct procedure when thyroidectomy or radioactive iodine therapy is the recommended therapy or as a primary therapy when surgical procedures is not recommended or long term therapy is advisabe.

8 Claims, No Drawings

TREATMENT OF HYPERTHYROIDISM WITH 1,3-DIHYDRO-1[2-(2-THIENYL)ALKYL]-2H-IMIDAZOLE-2-THIONES

This invention relates to a novel method for the treatment of hyperthyroidism by means of the administration of the dopamine beta-hydroxylase inhibitors which are derivatives of 1-(thienylalkyl)imidazole-2-thiol.

More specifically, this invention relates to the treatment of hyperthyroidism, either as a preparatory adjunct procedure when thyroidectomy or radioactive iodine therapy is the recommended therapy or as a primary therapy when surgical procedures are not recommended or long term therapy is advisable, through the administration of 1-(thienylalkyl)imidazole-2-thiol derivatives of the formula

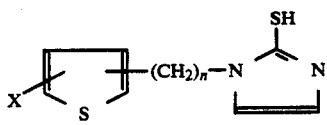

including the 2-thione tautomers thereof, wherein n is 1, 2, 3 or 4 and X is hydrogen, halogen or $C_{1-6}$ alkyl.

BACKGROUND OF THE INVENTION

As disclosed in U.S. Pat. No. 5,057,613, these compounds were previously known to show a dopamine betahydroxylase (DBH) inhibiting activity and to be useful in the treatment of hypertension at dosages of about 1 mg to 100 mg per kilogram body weight. Subsequent studies have shown that these compounds have a profound effect on the thyroid, rendering them useful for treating hyperthyroidism at doses equivalent to or lower than their blood pressure lowering dosages. Assays indicating the activity of compounds of this invention as DBH inhibitors and antihypertensive agents are described in U.S. Pat. No. 5,057,613, which is incorporated herein by reference.

It has now been discovered that the compounds of this invention are also potent antihyperthyroid agents. This activity is not normally associated with DBH inhibitors having antihypertensive activity. One compound combining antihyperthyroid activity with DBH inhibitory activity is methimazole (Tapazole®, Lilly). Methimazole, 1-methyl-2-mercaptoimidazole, is administered for treatment of hyperthyroidism in dosages of 15–60 mg/day divided into 3 doses for administration at 8-hour intervals (Physicians' Desk Reference, 1992). Studies by Ray W. Fuller, et al., (Advances in Enzyme Regulation, 1977, V15, pp. 267–281), have shown that methimazole's DBH-inhibiting activity is less pronounced than that of methimazole analogs bearing larger 1-alkyl substituents in place of the methyl group, while the greatest DBH inhibition was measured for 1-cyclohexyl-2-mercaptoimidazole (CHMI) which showed only slight antithyroid activity.

DETAILED DESCRIPTION OF THE INVENTION

As disclosed in U.S. Pat. No. 5,057,613, 1-(thienylalkyl)imidazole-2-thiol derivatives of the formula

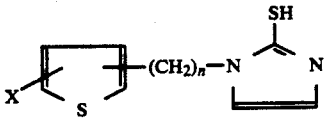

including the 2-thione tautomers thereof, wherein n is 1, 2, 3 or 4 and X is hydrogen, halogen or $C_{1-6}$ alkyl, were previously known to show a dopamine beta-hydroxylase inhibiting activity and to be useful in the treatment of hypertension at dosages of about 1 mg to 100 mg per kilogram body weight. Subsequent studies have shown that these compounds have a profound effect on the thyroid, rendering them useful for treating hyperthyroidism at doses equivalent to or lower than their blood pressure lowering dosages.

Formula I above shows the compounds of the present invention as thiols, but the compounds tautomerize readily to the corresponding 2-thiones and the two forms are considered as equivalent. Thus any description or reference to a 1,3-dihydro-2H-imidazole-2-thione should be considered as a description or reference to the corresponding 1H-imidazole-2-thiol or vice versa.

The "lower alkyl" groups referred to above are straight or branched-chain hydrocarbyl radicals having up to six carbon atoms, preferably methyl, ethyl and propyl; the halogen groups referred to above are illustrated by chloro, fluoro or bromo. The thienyl moiety is attached to the nitrogen atom of the imidazole moiety through an alkylene bridging moiety having one to four carbon atoms and such alkylene groups are illustrated by methylene, ethylene, trimethylene and tetramethylene. Those compounds in which n is 2 (i.e., the bridging group is ethylene) are preferred. The thienyl ring may be bonded to the alkyl chain through the 2- or 3- position, with the 2-position of thienyl ring being the preferred attachment. The preferred compound of this invention is 1,3-dihydro-1-[2-(2-thienyl)ethyl]-2H-imidazole-2-thione.

The activity of the compounds of Formula I is illustrated through their effects on thyroid function in the rat. At high doses, 1,3-dihydro-1-[2-(2-thienyl)ethyl]-2H-imidazole -2-thione has been discovered to cause lesions in the thyroid gland and associated clinicopathological findings that indicate thyroid hormone synthesis is reduced or inhibited. These findings suggest that the compound will be useful in the treatment of hyperthyroidism with the advantage that a single daily dose rather than divided daily dose administration will be sufficient therapy.

Two week rat studies indicated that the oral administration of the compound at doses of 50 to 700 mg/kg/day caused striking effects on the thyroid follicular epithelium with the onset of this effect being noticeable at three to four days. Sprague-Dawley rats were divided into groups of five males and five females and administered daily by gavage 0, 50, 100, 200, 300, 500, 700 and 1,000 mg/kg/day for two weeks under both fed and fasted conditions. Behavior of the rats was monitored daily while body weight, food consumption and clinical signs were measured weekly. At the termination of the study, rats were bled for clinical chemistry and hematology determinations. After bleeding, rats were sacrificed and necropsied in order that organs could be examined grossly, and tissue specimens were collected for subsequent microscopic examination.

At lower doses (100–300 mg/kg/day for males; 50–300 mg/kg/day for females), the thyroid follicular epithelium was mainly hypertrophic with minimal colloid involution. At doses of >500 mg/kg/day, thyroid follicular cell findings were detected consisting of diffuse hyperplasia, hypertrophy, increased mitotic FIGURES, and involution or total absence of luminal colloid. Collectively, these findings were given a morphologic diagnosis of thyroid follicular cell hyperplasia. Similar findings have been reported with compounds that cause the inhibition of iodination of thyroid hormones. In the rat, reduction in thyroid hormones has been shown to cause the increase production of pituitary thyroid stimulating hormone (TSH), whose stimulatory effect on thyroid follicular epithelium results in similar findings as observed with administration of 1,3-dihydro-1-[2-(2-thienyl)ethyl]-2H-imidazole-2-thione in the rat.

Elevated cholesterol levels (approximately 135% of pretest values) at doses >200 mg/kg/day in females and >500 mg/kg/day in males was an additional finding suggesting that thyroid function had been impaired. Hypercholesterolemia is a clinicopathologic finding frequently associated with reduced thyroid function.

An additional three month rat study demonstrated that single daily doses of 50 and 200 mg/kg/day of 1,3-dihydro-1-[2-(2-thienyl)ethyl]-2H-imidazole-2-thione caused profound thyroid effects characterized by thyroid follicular cell hyperplasia, increased thyroid weights and hypercholesteremia. Collectively, these findings are consistent with drug-induced inhibition of thyroid function and resulting morphological alterations due to compensatory stimulation of increased TSH due to decreased secretion of thyroid hormones.

For this study Sprague-Dawley rats were divided into groups of 33 males and 33 females and administered by gavage 0, 50 and 200 mg/kg/day of 1,3-dihydro-1-[2-(2-thienyl)ethyl]-2H-imidazole-2-thione in 0.5% aqueous methylcellulose for up to three months. Additional pharmacokinetic study of drug levels was performed by bleeding 3 males and 3 females from each group either 2 or 24 hours posdosing on treatment days 1, 45 and 87. Study parameters included daily observation of behavior; weekly observations of physical condition, food consumption and body weight; and terminal ophthalmoscopic evaluation, serum clinical chemistry, hematology, organ weights, and gross and microscopic tissue examinations.

Following one month recovery from dosing, these findings related to the thyroid gland were nearly completely reversible.

A summary of these observations is as follows:

| FINDING | Dose mg/kg/day | | | | | |
|---|---|---|---|---|---|---|
| | 0 | | 50 | | 200 | |
| | Male | Female | Male | Female | Male | Female |
| TREATMENT: | | | | | | |
| Thyroid Folicular Cell Hyperplasia (incidence) | 1/10 | 1/10 | 10/10 | 7/10 | 10/10 | 10/10 |
| Thyroid Weight (gm) | $.02 \pm .01^a$ | $.02 \pm .00$ | $.04 \pm .01^b$ | $.03 \pm .01^b$ | $.14 \pm .08^b$ | $.06 \pm .03^b$ |
| Serum Cholesterol (mg/dl) | 63 | 71 | 81 | 88 | 97 | 105 |
| RECOVERY: | | | | | | |
| Thyroid Folicular Cell Hyperplasia (incidence) | 0/5 | 0/5 | 0/5 | 0/5 | 0/5 | 8/10 |
| Thyroid Weight (gm) | $.02 \pm .01$ | $.01 \pm .00$ | $.03 \pm .01$ | $.02 \pm .00$ | $.05 \pm .01^c$ | $.03 \pm .01^b$ |
| Serum Cholesterol (mg/dl) | 75 | 66 | 74 | 86 | 76 | 76 |

$^a$Values represent mean ± standard deviation
$^b$P < 0.01 compared to controls
$^c$P < 0.05 compared to controls These results are indicative of the usefulness of compounds of Formula I in the chemical treatment of hyperthyroidism other than forms of hyperthryoidism such as Graves' disease that are caused by immune system disorders. The compounds are useful either as a preparatory adjunct procedure when thyroidectomy or radioactive iodine therapy is the recommended therapy or as a primary therapy when surgical procedures is not recommended or long term therapy is advisable.

Based on the foregoing test results, as well as by comparison with similar test results for compounds known to be useful, the compounds of this invention are expected to exhibit end-use antihyperthyroid activity at doses of about 0.5 mg to 100 mg per kilogram of body weight, preferably at doses of from 0.5 mg to 50 mg per kilogram of body weight. Although the compounds may be administered in from 2–4 divided doses during the day, it is preferred that the compounds be administered in a single daily dose.

As stated above, the compounds of this invention are useful in the treatment of hyperthyroidism. In the management of hyperthyroidism, the compounds of this invention may be utilized in compositions such as tablets, capsules or elixirs for oral administration, suppositories for rectal administration, sterile solutions or suspensions for parenteral or intramuscular administration, and the like. The compounds of this invention can be administered to patients (animals and human) in need of such treatment in dosages that will provide optimal pharmaceutical efficacy. Although the dose will vary from patient to patient depending upon the nature and severity of disease, the patient's weight, special diets then being followed by a patient, concurrent medication, and other factors which those skilled in the art will recognize, the dosage range will generally be about 0.5 to 100 mg per kilogram of patient body weight per day, which can be administered in single doses or multiple doses. Naturally these dose ranges can be adjusted on a unit basis as necessary to permit divided daily dosage and, as noted above, the dose will vary depending on the nature and severity of the disease, weight of patient, special diets and other factors.

Typically, these combinations can be formulated into pharmaceutical compositions according to standard procedures generally known in the art.

About 0.5 to 100 mg of a compound or mixture of compounds of Formula I is compounded with a physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

Illustrative of the adjuvants which may be incorporated in tablets, capsules and the like are the following: a binder such as gum tragacanth, acacia, corn starch or gelatin; an excipient such as microcrystalline cellulose; a disintegrating agent such as corn starch, pregelatinized starch, alginic acid and the like; a lubricant such as magnesium stearate; a sweetening agent such as sucrose, lactose or saccharin; a flavoring agent such as peppermint, oil of wintergreen or cherry. When the dosage unit form is a capsule, it may contain in addition to materials of the above type, a liquid carrier such as fatty oil. Various other materials may be present as coatings or to otherwise modify the physical form of the dosage unit. For instance, tablets may be coated with shellac, sugar or both. A syrup or elixir may contain the active compound, sucrose as a sweetening agent, methyl and propyl parabens as preservatives, a dye, and a flavoring such as cherry or orange flavor.

Sterile compositions for injection can be formulated according to conventional pharmaceutical practice by dissolving or suspending the active substance in a vehicle such as water for injection, a naturally occurring vegetable oil like sesame oil, coconut oil, peanut oil, cottonseed oil, etc., or a synthetic fatty vehicle like ethyl oleate or the like. Buffers, preservatives, antioxidants and the like can be incorporated as required.

In the preparation of the compounds of this invention it is quite obvious that the specific compound sought to be prepared will have a bearing on the particular process path to be utilized. Such factors as the specific X substituent, the particular alkylene bridge present between the imidazolyl moiety and its attached thienyl moiety, and ready availability of the starting materials all play a role in choosing the specific path to be followed in the preparation of the compounds of this invention. Those factors are readily appreciated by one of ordinary skill in the art. However, in general, the compounds of this invention may be prepared by standard techniques and processes analogously known in the art.

To prepare compounds which contain a sulfhydryl substituent on the imidazole ring moiety, it is convenient to react an isothiocyanate derivative (II) with an appropriate amino acetal (III) to form a thiourea reaction product (IV), which is treated with acid to hydrolyze the acetal whereupon a cyclization reaction takes place to form the imidazole ring bearing the sulfhydryl substituent (I). These reactions are depicted in Reaction Scheme A in which (III) is shown as the methyl acetal although, obviously, the ethyl acetal could also be used.

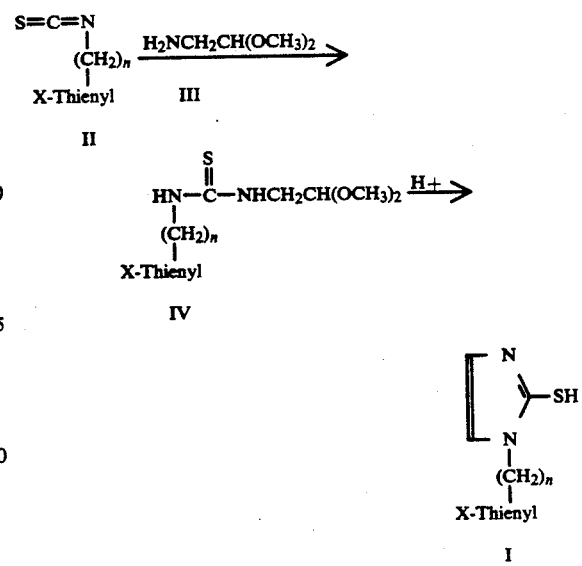

wherein n and X are as defined in formula I.

The reaction of the isothiocyanate derivatives (II) with the acetal (III) is a simple condensation reaction, preferably effected by heating the reactants under reflux conditions using inert solvents, e.g., toluene or DMF at 80° C., to form the thiourea (IV) intermediates. These intermediates are subjected to cyclization by treatment with acid, preferably by refluxing the intermediates with aqueous hydrochloric acid in ethanol to produce the desired 1-substituted-2-imidazole bearing a sulfhydryl substituent (Ia).

The present 1-thienyl-2-imidazoles (Ic) may also by prepared by treating a thienylaldehyde derivative (V) with the aforementioned acetals (III) to form a Schiff base which is reduced to form an intermediate (VI) which is subjected to a cyclization reaction by treatment with aqueous HCl in ethanol in the presence of an alkali metal isothiocyanate, preferably KSCN. These reactions may be depicted by the following reaction scheme.

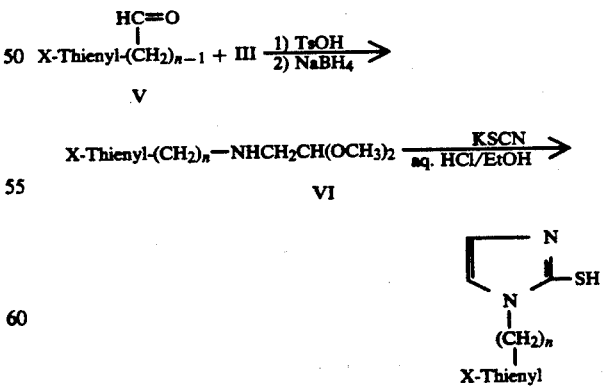

wherein X and n are defined as above.

The isothiocyanates used as the starting materials in Reaction Scheme A are prepared by the reaction of the appropriate amine with 1,1'-thiocarbonyldiimidazole. The amine used can, in turn, be obtained by reduction of the corresponding nitrile. Diborane is a useful reagent for the reduction of such a nitrile. The nitrile itself can be obtained by the reaction of an alkali metal cyanide with a compound of the formula X-Thienyl-(CH$_2$)$_{n-1}$—Q wherein X and n are defined as above and Q is a 4-toluenesulfonyloxy or a similar leaving group or a halogen such as chloro or bromo. The indicated sulfonyloxy compounds are obtained by the reaction of the appropriate alcohol and sulfonyl chloride.

The following examples merely illustrate the various techniques and procedures utilized for the preparation of the compounds useful in this invention; it being understood that they are not meant to limit the scope of the compounds defined by this invention.

EXAMPLE 1

1,3-Dihydro-1-(2-thienylmethyl)-2H-imidazole-2-thione

A mixture of 33.6 g (0.3 mol) thiophene-2-carboxaldehyde, 39.9 g (0.3 mol) aminoacetaldehyde diethyl acetal, 0.3 g of 4-toluenesulfonic acid (TsOH) and 200 ml ethanol is placed in a 500 ml flask and heated to reflux. After 2 hours, the reaction is concentrated and the residue dissolved in 250 ml ethanol. Solid NaBH$_4$ (12.5 g, 0.33 mol) is added in small portions. The reaction is refluxed for 1-½ hours, cooled to room temperature and poured into cold water. The product is extracted into CH$_2$Cl$_2$ (2×250 ml). After drying (Na$_2$SO$_4$) and concentration, 66.7 g crude product is obtained as a pale yellow oil. 22.9 g (0.1 mol) of the crude amine is placed in a 500 ml flask along with 11.7 g (0.12 mol) KSCN, 150 ml ethanol, 40 ml water and 15 ml concentrated hydrochloric acid. After refluxing for 5 hours, the reaction is poured onto 1 liter of ice water. The white crystals are collected and dried to give 12.0 g (61%) product, mp 128°-130° C. (EtOH).

EXAMPLE 2

1,3-Dihydro-1-(2-thienylmethyl)-2H-imidazole-2-thione

Under a blanket of nitrogen, 11.3 g (0.1 mol) 2-aminomethylthiophene is added to 19.6 g (0.11 mol) 1,1'-thiocarbonyldiimidazole in 200 ml anhydrous toluene at 0° C. the reaction is held at 0° C. for 4 hours. Then 10.5 g (0.1 mol) aminoacetaldehyde dimethyl acetal is added and the reaction is warmed at 80° C. for 2 hours. The toluene is removed and the residue dissolved in 100 ml ethanol, 15 ml water and 15 ml concentrated HCl. The mixture is refluxed 5 hours, cooled and poured into 1L ice. After recrystallization (1/1 EtOH/H$_2$O) the desired product is obtained as white shiny crystals, mp 128°-130° C.

In a similar manner, by following the generic teachings related to Reaction Schemes A or B and by substantially following the procedures of the foregoing examples, there may be prepared the following 1,3-dihydro-2H-imidazole-2-thiones:

1-(5-chloro-2-thienylmethyl)-1,3-dihydro-2H-imidazole-2-thione, 1-(5-bromo-2-thienylmethyl)-1,3-dihydro-2H-imidazole-2-thione, 1-(5-methyl-2-thienylmethyl)-1,3-dihydro-2H-imidazole-2-thione, The corresponding 1-[2-(2-thienyl)ethyl], 1-[3-(2-thienyl)propyl], and 1-[4-(2-thienyl)butyl]homologs are likewise obtained in a similar way.

EXAMPLE 3

1,3-Dihydro-1-[3-(2-thienyl)propyl]-2H-imidazole-2-thione

A mixture was prepared from 20.8 g of 2-[2-(4-toluenesulfonyloxy)ethyl]thiophene, 5.4 g of sodium cyanide and 175 ml of dimethylsulfoxide and this mixture was heated to 90° C. The mixture was quenched by pouring it into saturated aqueous ammonium chloride solution and the resulting solution was extracted into ethyl acetate. The ethyl acetate solution was dried over sodium sulfate and the solvent was evaporated under reduced pressure to give crude 2-thiophenepropionitrile. This product was mixed with 175 ml of 1M diborane in tetrahydrofuran and allowed to stir at room temperature. The reaction was quenched in ethanol and methanolic hydrogen chloride was added. The white solid which formed was separated by filtration, washed with ether and dried in a vacuum oven to give 3-(2-thienyl)propylamine hydrochloride melting at about 197-°198° C.

A solution of 4.1 g of 3-(2-thienyl)propylamine (obtained from the hydrochloride by standard procedures) in about 100 ml of dimethylformamide was cooled to 0° C. and 5.7g of solid 90% 1,1'-thiocarbonyldiimidazole was added. The mixture was allowed to warm slowly to room temperature and then stirred for 16 hours. It was then poured into water and the resulting aqueous mixture was extracted with three portions of ethyl acetate. Saturated sodium chloride solution was added to break up any emulsion. The resulting ethyl acetate solution was washed with water, dried over sodium sulfate and then concentrated. The crude product obtained was mixed with 3.0 g of aminoacetaldehyde dimethyl acetal in 80 ml of dimethylformamide and heated at 80° C. for 3 hours. The mixture was then cooled to room temperature and the solvent was removed under reduced pressure. The residue was dissolved in ethanol and 2.5N hydrochloric acid was added to hydrolyze the acetal. The mixture was heated at reflux for 2 hours and then cooled to room temperature and poured into 500 g of ice. The resulting mixture was then heated to remove any remaining ethanol but no solid formed in the residual mixture which was then extracted with three portions of ethyl acetate. The ethyl acetate extracts were combined and dried over sodium sulfate and the solvent was evaporated to give a residual tan oil. This oil crystallized on standing and was recrystallized from toluene to give 1,3-dihydro-1-[3-(2-thienyl)propyl]-2H-imidazole-2-thione melting at about 94°-96.5° C.

EXAMPLE 4

1,3-Dihydro-1-[2-(2-thienyl)ethyl]-2H-imidazole-2-thione

To 4,000 ml of 1M diborane/tetrahydrofuran there was added 170 g of 2-thiopheneacetonitrile over a period of 30 minutes. The reaction temperature gradually warmed to 47° C. during the addition and the mixture was then allowed to cool to room temperature and stand and stir for 5 days. The colorless reaction was quenched by the addition of 800 ml of ethanol followed by 300 ml of saturated methanolic hydrogen chloride until the mixture became acidic. The solid which precipitated from the solution was collected by filtration, washed with ether and then dried in a vacuum oven at 50° C. to give 2-(2-thienyl)ethylamine hydrochloride melting at about 198°-200° C.

2-(2-Thienyl)ethylamine (91 g, obtained by partitioning the hydrochloride salt between ethyl acetate and ice cold 2N sodium hydroxide, washing the organic layer with brine, drying with sodium sulfate and evaporating the solvent in vacuo to a colorless oil) in 500 ml of dimethylformamide was added all at once to an ice cooled solution of 142 g of 90% 1,1'-thiocarbonyldiimidazole in dimethylformamide. The mixture was stirred for 16 hours at room temperature and then poured into 4,000 ml of brine. The resulting solution was extracted with three portions of ethyl acetate and the combined organic layers were washed with water and dried over sodium sulfate and the solvent was evaporated to leave a residual oil which was the isothiocyanate corresponding to the starting amine. To a solution of 194 g of this crude isothiocyanate in 300 ml of dimethylformamide there was added 75 g of aminoacetaldehyde dimethyl acetal. The reaction warmed to 70° C. and was further heated at 80° C. for 2.5 hours. After the mixture was cooled to room temperature, the dimethyl-formamide was removed by Kugelrohr distillation. The residual orange oil was mixed with 500 ml of 10% aqueous hydrochloric acid and 300 ml of ethanol and heated at a gentle reflux for 2 hours. The resulting solution was cooled and poured onto 3 liters of ice with stirring. Crystallization was induced by the addition of a seed crystal and the solid which formed was separated by filtration and dried in a vacuum oven at 50° C. It was then recrystallized from toluene to give 1,3-dihydro-1-[2-(2-thienyl)ethyl]-2H-imidazole-2-thione melting at about 131°-134° C. This compound has the following structural formula:

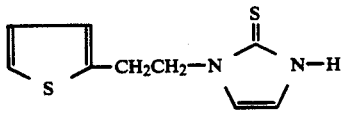

EXAMPLE 5

If the appropriate alcohol is used as the starting material and it is reacted with 4-toluenesulfonyl chloride to give the corresponding sulfonate ester which is then further reacted according to the procedure described in Example 4, or the appropriate nitrile is used as the starting material and it is further reacted according to the procedures described in Examples 3 or 4, the following compounds are obtained:

1,3-Dihydro-1-[2-(5-chloro-2-thienyl)ethyl]-2H-imidazole-2-thione.

1,3-Dihydro-1-[2-(5-bromo-2-thienyl)ethyl]-2H-imidazole-2-thione.

1,3-Dihydro-1-[2-(5-methyl-3-thienyl)ethyl]-2H-imidazole-2-thione.

1,3-Dihydro-1-[2-(2-methyl-3-thienyl)ethyl]-2H-imidazole-2-thione.

1,3-Dihydro-1-[4-(5-methyl-2-thienyl)butyl]-2H-imidazole-2-thione.

What is claimed is:

1. A method for the treatment of hyperthyroidism which comprises administering to a patent in need thereof an effective dose of a compound represented by the formula:

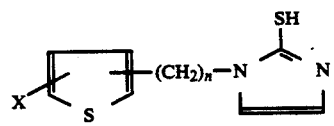

including the 2-thione tautomers thereof, in which X is hydrogen, halogen or $C_{1-6}$ alkyl and n is 1, 2, 3 or 4.

2. A method according to claim 1 wherein n is 2.

3. A method according to claim 1 wherein X is hydrogen.

4. A method according to claim 1 wherein the compound is 1,3-dihydro-1-[2-(2-thienyl)ethyl]-2H-imidazole-2-thione.

5. A method according to claim 1 wherein the compound is 1,3-dihydro-1-[2-(2-thienyl)propyl]-2H-imidazole-2-thione.

6. A method according to claim 1 wherein the compound is administered at a dosage of from 0.5-100 mg/kg/day.

7. A method according to claim 1 wherein the compound is administered at a dosage of from 0.5-50 mg/kg/day.

8. A method according to claim 1 wherein the compound is administered in a single daily dosage.

* * * * *